(12) United States Patent
Heutschi

(10) Patent No.: US 8,622,956 B2
(45) Date of Patent: Jan. 7, 2014

(54) INJECTION DEVICE WITH SIMPLIFIED STOPPER RETENTION

(75) Inventor: Ivan Heutschi, Grosshochstetten (CH)

(73) Assignee: Roche Diagnostics International AG, Rotkreuz (CH)

(*) Notice: Subject to any disclaimer, the term of this patent is extended or adjusted under 35 U.S.C. 154(b) by 879 days.

(21) Appl. No.: 12/392,425

(22) Filed: Feb. 25, 2009

(65) Prior Publication Data

US 2009/0247957 A1 Oct. 1, 2009

Related U.S. Application Data

(63) Continuation of application No. PCT/EP2007/003485, filed on Apr. 20, 2007.

(30) Foreign Application Priority Data

Aug. 30, 2006 (EP) .................................. 06119779

(51) Int. Cl.
*A61M 37/00* (2006.01)
*A61M 5/315* (2006.01)

(52) U.S. Cl.
USPC ............... 604/89; 604/220; 604/218; 604/82; 604/90

(58) Field of Classification Search
USPC .......... 604/218–222, 232, 233, 82, 85, 89–92
See application file for complete search history.

(56) References Cited

U.S. PATENT DOCUMENTS

| | | | | |
|---|---|---|---|---|
| 4,235,235 A | * | 11/1980 | Bekkering | 604/238 |
| 5,080,649 A | * | 1/1992 | Vetter | 604/91 |
| 5,236,420 A | * | 8/1993 | Pfleger | 604/122 |
| 5,352,196 A | * | 10/1994 | Haber et al. | 604/90 |
| 2002/0016572 A1 | | 2/2002 | Beebe | |
| 2005/0043689 A1 | | 2/2005 | Chen | |
| 2005/0240159 A1 | * | 10/2005 | Kito et al. | 604/222 |
| 2006/0173409 A1 | | 8/2006 | Yang | |

* cited by examiner

*Primary Examiner* — Emily Schmidt
*Assistant Examiner* — Bradley G Thomas, Jr.
(74) *Attorney, Agent, or Firm* — Dinsmore & Shohl LLP (57) ABSTRACT

An injection device including a volume for accommodating a product for administration, a piston for acting upon the product within the volume, and a stopper which can be arranged between an end of the piston facing the product and the product within the volume, wherein the piston includes a piston head configured to be sealed in a gas-tight manner, the piston head being separate from the stopper such that a negative pressure or vacuum region can be developed between the piston head and the stopper.

18 Claims, 3 Drawing Sheets

INJECTION DEVICE WITH SIMPLIFIED STOPPER RETENTION

CROSS-REFERENCE TO RELATED APPLICATIONS

This application is a continuation of International Patent Application No. PCT/EP2007/003485, filed on Apr. 20, 2007, which claims priority to European Application No. 06119779.4, filed on Aug. 30, 2006, the entire contents of both of which are incorporated herein by reference.

BACKGROUND

The present invention relates to devices for administering, delivering, injecting or dispensing substances, and to methods of making and using such devices. More particularly, it relates to such devices, including, for example, injection devices, injection pens, etc., for dispensing medicinal substances, such as insulin or hormones, in selected amounts or doses. More particularly, the present invention relates to an injection device with a volume for accommodating a product or substance for administration, with a piston to act upon the product within the volume, and with a stopper which can be arranged between the end of the piston facing the product and the product within the volume.

SUMMARY

Various infusion devices that provide for retention of an inserted stopper via a thread or an overpressure valve are known. Such known devices are relatively expensive to manufacture and pose safety risks due to awkward handling requirements. It some embodiments, the present disclosure aims to at least partially eliminate disadvantages associated with such known devices.

In one embodiment, the present invention is directed to an injection device with a retention or retaining feature for an inserted stopper which is relatively easy to construct and, which, therefore is less expensive relative to known devices.

In one embodiment, the present invention comprises an injection device comprising a volume or substance containing space for accommodating a substance or product to be administered, a piston for acting upon the product within the volume, and a stopper which can be arranged between an end of the piston facing the product and the product within the volume, wherein the piston includes a piston head configured to be sealed in a gas-tight manner, the piston head being separate from the stopper such that a negative pressure or vacuum region can be developed between the piston head and the stopper.

In one embodiment, the present disclosure is directed to an injection device that is easy to handle.

In one embodiment of the present invention, a piston is provided with a piston head which can be sealed in a gas-tight manner and which is separate from the stopper such that a negative pressure or vacuum region can be developed between the piston head and the stopper.

In one embodiment, the stopper retention may therefore be effected by generating a negative pressure or a vacuum. While the stopper is moved forward in the usual way by the piston head, the negative pressure region or vacuum region between the stopper and the piston head prohibits an unintended movement of the stopper, since the negative pressure in the intermediate space would be intensified by a movement of the stopper without a participating movement of the head. Thus, an unintended separate movement of the stopper is either substantially reduced or damped or, if low forces or forces that are not too great act on the stopper, such unintended movements are prevented from the outset.

In one embodiment, if a patient is connected via a conventional injection device and an associated infusion set to a supply, different forces can act on the stopper. These potential forces include a negative pressure in the environment relative to the pressure in the volume of the injection device, and the hydrostatic pressure caused by the height difference between the puncture site of the infusion set on the body of the patient and the injection device.

In one embodiment, additional frictional forces may arise between the volume wall of the injection device and the stopper. These frictional forces can vary greatly, such that genuinely reproducible administration parameters are not available. While in one injection device the stopper may experience no unintended displacement at relatively high forces, which are exerted on it by the environment, in other similarly designed injection devices an unintended displacement can easily occur in the same environment.

In one embodiment, the negative pressure or vacuum region provided between the stopper and the piston head may make available a range of forces in order to secure the stopper against the attacking forces, so as to be able to avoid an unintended administration of a medicament or product.

In one embodiment, the piston head comprises a sealing lip which extends about the full circumference and which provides a gas-tight seal with respect to the volume wall. In this way, the piston head can be moved to and fro, allowing a vacuum or negative pressure region to develop between the stopper and the piston head. On the other hand, it is also possible to design the piston head with a sufficiently exact fit without sealing lip, such that it can provide a seal with respect to the volume wall in order to be able to develop a negative pressure or a vacuum between the stopper and the head.

In one embodiment, if a sealing lip is provided, the latter can advantageously have a predetermined leakage arrangement counter to the direction of insertion of the piston head. In an illustrative embodiment, when the piston head is pushed into the volume, the sealing lip is able to snap round counter to the direction of insertion of the piston head and thus cause a leakage by which air or gas inside the free volume can escape, i.e. until the piston head hits the stopper. If, after the head has hit the stopper, the piston head is then pulled, a negative pressure region is set up, the sealing lip being suitably designed on its outer circumference such that it can provide a sealing action. The sealing lip can be provided, for example on the edge or near the edge of its side facing toward the stopper, with a structure, for example a radially extending groove structure, which does not extend through the sealing lip in the axial direction of the sealing lip or of the piston head.

In one embodiment, to generate the vacuum between the stopper and the piston head, it does not have to be necessary to pull on the piston head, i.e. no reverse movement of the piston head is needed to generate the vacuum. A folding around of the sealing lip may be needed to release the piston head from the stopper, since in this way air can flow into the space and the vacuum is thus lost or the connection between stopper and piston head broken.

In one embodiment, it is also possible for the piston rod, on which the piston head is secured, to be designed in such a way that the overpressure occurring upon insertion of the piston head can escape through it. For example, the piston rod can be made partly hollow or can be designed with an inner conduit that is able to open and close, such that an overpressure can escape via the piston rod. After the overpressure has escaped, the conduit is closed, for example by means of a stopper, a valve, a film or the like, such that upon subsequent loading of the stopper or of the piston head an unintended displacement of the stopper can be avoided by the developing low pressure.

In one embodiment, the piston head may be designed with another type of sealing arrangement, for example a separate or integrally formed O-ring. This O-ring is then also able to provide a seal with respect to the wall of the volume.

Moreover, in one embodiment, such a head or a head per se according to the present invention can also be designed with at least one valve. Such a valve can be provided, for example, in the form of a one-way valve, i.e. the valve opens when the piston head is inserted into the volume, such that an overpressure can escape. After the overpressure has escaped or when the piston rod is pulled, the one-way valve closes and a vacuum can be developed between the head and the stopper, which, as has been explained above, can perform its positive effects. The valve can prevent air from flowing into the vacuum. In this way, displacement, however small, of the stopper can result in a negative pressure in the volume, which acts against potentially attacking forces such as negative pressure in the environment or hydrostatic pressure forces. The greater the unintended displacement of the stopper away from the piston, the greater is the counterforce that is built up by the negative pressure and that moves the piston back to the starting position.

In some embodiments, the valve arrangement can also be in the form of a two-way valve, in particular when the latter is designed with different trigger pressures. Thus, the trigger pressure upon insertion of the piston head can be set lower than the trigger pressure upon withdrawal of the piston head. The trigger pressure upon withdrawal and the retention force tying or after use and to use another volume or container with fresh product or medicament or the like and to use the same piston head, optionally after a cleaning procedure, e.g. in a new volume or with a new ampoule.

In one embodiment, the stopper can be formed with a cavity that is located in the axial direction of the stopper opposite the piston head to favor the inverting movement of the sealing lips, wherein the negative pressure region is formed between head and stopper.

In one embodiment, two valves corresponding to the abovementioned two-way valve can also be dimensioned and provided separately, instead of a single two-way valve with the aforementioned features.

In one embodiment of a valve arrangement for the device according to the present invention, a through-opening of a valve is closed with a membrane which can be moved freely or with limited freedom in the air or gas outlet direction, while the membrane is supported in the air inlet direction. By the support in the air inlet direction, a sealing contact for membrane support can be achieved, i.e. to the environment of the valve opening, such that a sufficient negative pressure or vacuum pressure can be developed between the stopper and the piston head.

According to the present invention, it has been found that a smaller negative pressure or vacuum region between piston head and stopper leads to a greater retention force for the stopper, which acts against unintended displacement of the stopper. The table below provides examples of retention forces (F) upon displacement (dX) of the stopper, with the piston head stationary.

| $V_0[mm^3]$ | $P_0[N/mm^2]$ | $A_{ampule}[mm^2]$ | $dX[mm]$ | $V_1[mm^3]$ | $P_1[N/mm^2]$ | $dp[N/mm^2]$ | $F[N]$ | $V_{error}[mm^3]$ | $V_{error}[IU]$ |
|---|---|---|---|---|---|---|---|---|---|
| 0 | 0.1 | 80 | 0.1 | 8 | 0.00 | 0.10 | 8.00 | 8 | 0.8 |
| 5 | 0.1 | 80 | 0.1 | 13 | 0.04 | 0.06 | 4.92 | 8 | 0.8 |
| 10 | 0.1 | 80 | 0.1 | 18 | 0.06 | 0.04 | 3.56 | 8 | 0.8 |
| 20 | 0.1 | 80 | 0.1 | 28 | 0.07 | 0.03 | 2.29 | 8 | 0.8 |
| 0 | 0.1 | 80 | 0.2 | 16 | 0.00 | 0.10 | 8.00 | 16 | 1.6 |
| 5 | 0.1 | 80 | 0.2 | 21 | 0.02 | 0.08 | 6.10 | 16 | 1.6 |
| 10 | 0.1 | 80 | 0.2 | 26 | 0.04 | 0.06 | 4.92 | 16 | 1.6 |
| 20 | 0.1 | 80 | 0.2 | 36 | 0.06 | 0.04 | 3.56 | 16 | 1.6 |
| 0 | 0.1 | 80 | 0.5 | 40 | 0.00 | 0.10 | 8.00 | 40 | 4 |
| 5 | 0.1 | 80 | 0.5 | 45 | 0.01 | 0.09 | 7.11 | 40 | 4 |
| 10 | 0.1 | 80 | 0.5 | 50 | 0.02 | 0.08 | 6.40 | 40 | 4 |
| 20 | 0.1 | 80 | 0.5 | 60 | 0.03 | 0.07 | 5.33 | 40 | 4 |
| 0 | 0.11 | 80 | 0.1 | 8 | 0.00 | 0.10 | 8.00 | 8 | 0.8 |
| 5 | 0.11 | 80 | 0.1 | 13 | 0.04 | 0.06 | 4.62 | 8 | 0.8 |
| 10 | 0.11 | 80 | 0.1 | 18 | 0.06 | 0.04 | 3.11 | 8 | 0.8 |
| 20 | 0.11 | 80 | 0.1 | 28 | 0.08 | 0.02 | 1.71 | 8 | 0.8 |

$V_0$: volume of hollow space after complete insertion of the head into the ampule/to the stopper
$p_0$: pressure in the hollow space after complete insertion of the head into the ampule/to the stopper
$A_{ampule}$: inner cross-sectional surface area of the ampule
dX: distance (in addition to $V_0$) between the stopper and the head (unintended displacement of the stopper)
$V_1$: volume of the hollow space after displacement by dX
$p_1$: pressure in the hollow space after the unintended displacement of the stopper by dX
dp: pressure difference p1 with respect to the ambient pressure (assuming $p_{ambient}$ = 1 bar)
F: force that results from the pressure difference and keeps the stopper from unintended slipping forward
$V_{error}$: unintentionally discharged volume (by dX)

to be applied thereby is greater than the maximum potential environmental tensile forces acting on the stopper.

In this way, in some embodiments, it is possible for a reusable injection device having the features according to the present invention to be made easy to reuse. When the higher pressure of the two-way valve has been overcome, the piston head can be pulled out using the piston rod, and the volume or substance containing area can be cleaned to be able to reuse the whole device according to the present invention. It is also possible to dispose of the volume with the stopper after emp- It is to be appreciated that the parameters and parameter values shown above are provided by way of illustration only and that the parameters and parameter values may be varied as suitable in accordance with various embodiments of the present invention.

In one embodiment, the retaining force, which can be effected according to the present invention by the vacuum or corresponding negative pressure that can be developed between the stopper and the head, may also depend on other parameters, for example the cross section of the ampule, i.e.

the cross section of the volume with the product to be administered, and the volume of the negative pressure or vacuum region prior to displacement of the piston head, this volume being designated as $V_0$. The pressure $p_0$ in the negative pressure or vacuum region prior to displacement may also play a role. In one embodiment, the air in the negative pressure or vacuum region is able to escape easily when the head is inserted.

In one embodiment, if the stopper in a device according to the present invention is displaced by a distance dX shown in the table, a volume $V_{error}$ of a medicament or the like is accidentally administered to the patient. The stopper can only be displaced here unintentionally if the pressure in the front part of the liquid path for delivering the medicament or the product is lower than the pressure in the negative pressure or vacuum region. This lower force can occur in the front part of the liquid path on account of forces that act on the overall force diagram, for example the negative pressure in the environment or the hydrostatic pressure in the whole infusion set. Moreover, to ensure that the stopper moves forward, the stopper friction also has to be overcome.

The table provided above has been drawn up on the premise that the cross-sectional surface area of the volume container the product or substance to be delivered amounts to approximately 80 mm$^2$, wherein a negative pressure in the environment of the device according to the present invention is in a range of ±150 mb, which can result in an additional force of ±1.2 Nmax. The hydrostatic pressure can be approximately ± 0.8 N with 1 m liquid column in the infusion set. Accordingly, in one embodiment, if the retaining forces, which can be applied by the negative pressure or vacuum region between the piston head and the stopper, at least slightly exceed the attacking forces varying in an area, the unintended displacement and thus an unintended administration of a medicament cannot take place.

It should be appreciated that any of the embodiments, features, functions and/or structures described herein may be used cooperatively and/or to complement each other.

BRIEF DESCRIPTION OF THE DRAWINGS

FIG. 2b is a perspective side view of the piston head of FIG. 2a;

FIG. 5b is a perspective side view of the piston head of FIG. 5a; and

FIGS. 6a to 6f show an embodiment of a valve arrangement in a piston head according to the present invention, wherein FIGS. 6a, 6c and 6e are axial sectional views and FIGS. 6b, 6d and 6f are plan views, in schematic form.

DETAILED DESCRIPTION

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making the invention and/or its components may be selected from appropriate materials such as metal, metallic alloys, ceramics, plastics, etc.

Figure 1A:
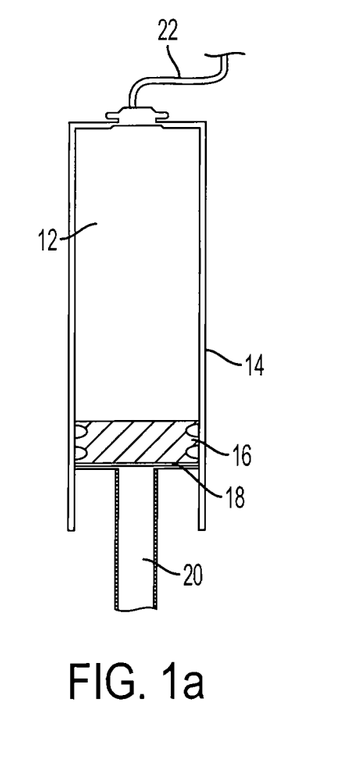
FIG. 1a is a schematic view of an embodiment of an infusion set or injection device having features according to the present invention, in an axial longitudinal section.

FIG. 1a depicts a product, substance or medicament 12 accommodated within a containing volume 14 that is able to deliver the medicament 12 to a patient via a delivery means, e.g. an infusion set 22. At the lower end of the volume 14, which may be a cylindrical ampoule, a stopper 16 is accommodated in the interior thereof, said stopper 16 providing a liquid-tight and air-tight seal with respect to the wall of the volume 14. Adjacent to the stopper 16 there is a piston head 18, on which a piston rod 20 is centrally mounted. The overall configuration may have a cylinder symmetry, but can configured in any shape. The piston head 18 is in direct contact with the stopper 16.

Figure 1B:
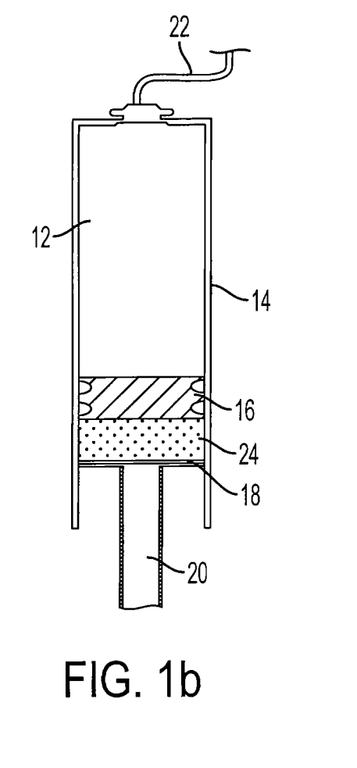
FIG. 1b is the view according to FIG. 1a, with a negative pressure or vacuum region indicated.

FIG. 1b depicts the device of FIG. 1a, whereby a force has been applied to the piston rod 20. The piston head 18 has thus been drawn away from the stopper 16, and a negative pressure or vacuum region 24 has developed between the piston head 18 and the stopper 16, which region, for purposes of illustration, is shown larger than it would actually be.

Figure 2A:
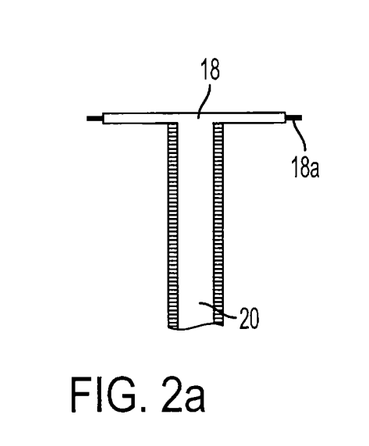
FIG. 2a shows an embodiment of a piston head having features according to the present invention, in an axial sectional view.
Figure 2B:
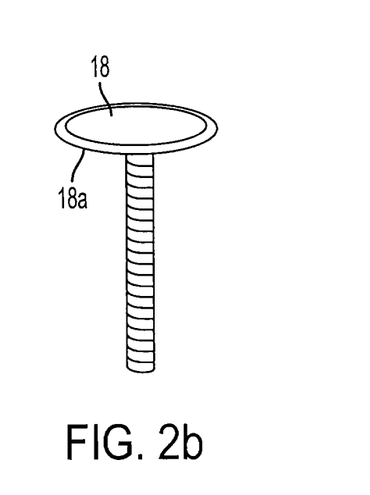

FIG. 2a shows one embodiment of a head or piston head 18 on which a stopper 16 is once again mounted. A lip or sealing lip 18a is arranged about the full circumference of the piston head. This sealing lip 18a can perform its sealing action between the head 18 and the wall of the volume 14. The arrangement of the sealing lip 18a about the full circumference can be seen better still from FIG. 2b. The piston rod can be designed with a thread such that, by rotation of the piston rod 20 designed as a threaded rod, the piston head 18 can be driven forward, or, by rotation in the opposite direction, the piston head 18 can be drawn back. The sealing lip 18a provided about the full circumference can perform its sealing function in each case.

FIG. 3 depicts insertion of a piston head into an injection device in various operating stages, according to some embodiments of the present invention. FIG. 3a depicts the piston head 18 outside the volume 14, and the sealing lip 18a therefore not yet in contact with the inner surface of the wall of the volume 14. A region 23 indicates that that there is still an air volume 14 here within the volume 14. According to FIG. 3b, the piston head 18 is now inserted into the volume 14, and the sealing lip 18a' now deforms counter to the direction of advance of the piston rod 20. In this state of deformation, the sealing lip 18a' is permeable only to gas outflow, such that the air can escape from the volume 23. According to FIG. 3c, the piston head finally comes into contact with the stopper 16, and the advance movement of the piston head 18 ends in this position. The sealing lip 18a', deformed in its open position, has now let almost all of the air out of the region 23, which is now no longer present. In this state of deformation, the sealing lip is tight against entry of air into the vacuum region.

Figure 3A:
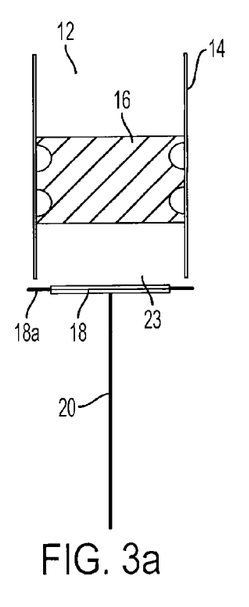
FIGS. 3a to 3e show, in schematic sectional views, the actuation of an embodiment of an injection device according to the present invention in different operating stages.
Figure 3B:
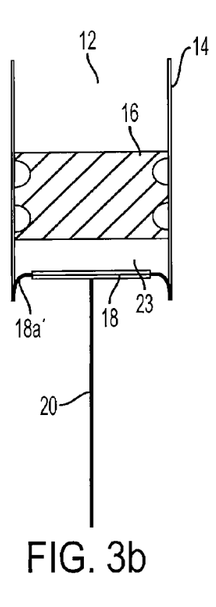
Figure 3C:
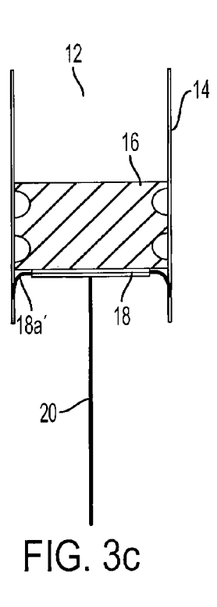
Figure 3D:
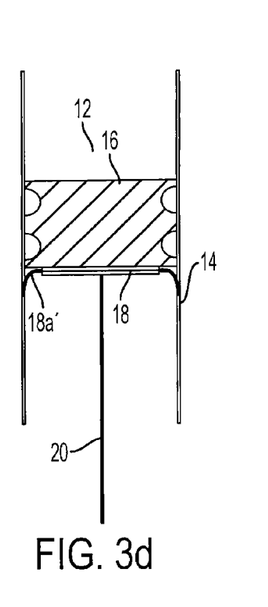
Figure 3E:
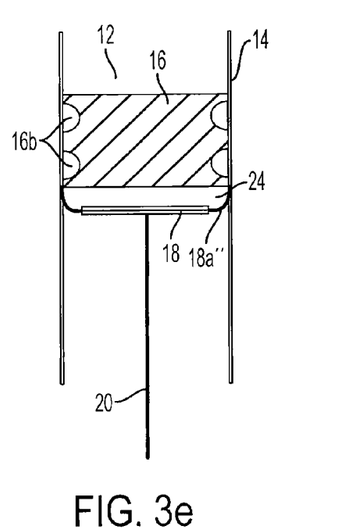

After the emptying and for removal of the volume, the piston rod 20 is pulled according to FIG. 3*d*, specifically counter to the direction of insertion. As soon as the tensile force exceeds a critical value, the sealing lip 18*a'* snaps round from its position oriented counter to the direction of insertion according to FIG. 3*d* and into a position according to FIG. 3*e*. The sealing lip 18*a'* now provides a nonsealing surface for air flowing into the vacuum region and thus permits release of the piston head from the stopper.

Figure 4:
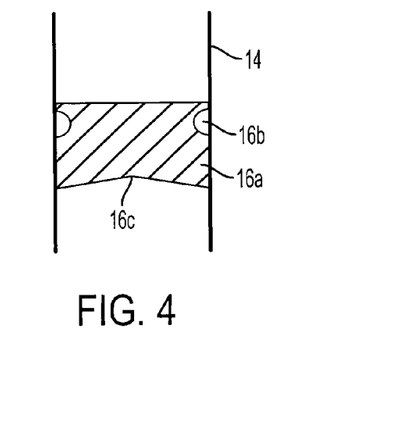
FIG. 4 is an axial sectional view of an embodiment of a stopper according to the present invention.

FIG. 4 shows a stopper 16*a* shaped in accordance with one embodiment of the present invention. The geometry of the stopper 16*a* is such that the sliding of the stopper into the volume generates much lower forces than its withdrawal. This permits reliable and simple removal of the piston head. In FIG. 4, the head comes from below to bear partially on the stopper 16*a*, while the product that is to be administered is stored above the stopper.

In some embodiments, the stopper 16*a* can have one or more radial indentations 16*b* to reduce the friction between the wall of the volume 14 and the stopper 16*a*. An additional sealing action can also be applied via edges between the indentations 16*b* and the wall of the volume 14. A cavity 16*c* can be provided in the stopper facing the piston head 18 (not shown in FIG. 4) in order to aid the development of the negative pressure region 24.

Figure 5A:
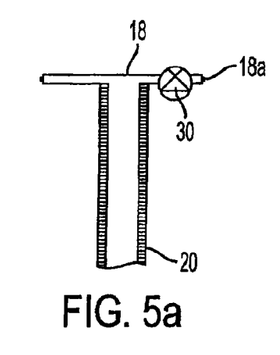
FIG. 5a is an axial sectional view of another embodiment of a piston head having features according to the present invention.
Figure 5B:
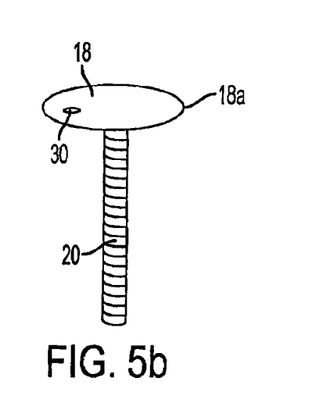
Figure 5C:
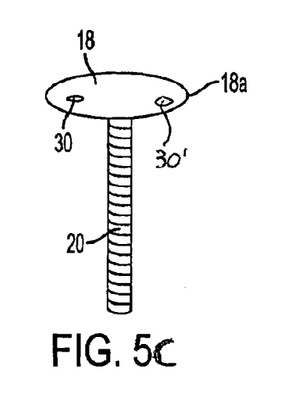
FIG. 5c is a perspective view of a piston head having two valves.

FIG. 5*a* shows an alternative form of the piston head 18 with piston rod 20. As shown, one or more valve arrangements 30 may be built into the head. The valve arrangements 30 may be one-way valves or two-way valves. A sealing action is made available by an integrally formed or separately provided O-ring seal 18*a*. The position of the valve 30 can be seen from FIG. 5*b*, as well as FIG. 5C, which depicts a first valve 30 and a second valve 30'. For example, with respect to FIG. 5C, the first valve 30 may be active in a first direction, and the second valve 30' may be active in a second direction, which is generally opposite the first direction.

It is of course also possible to make the piston rod 20 hollow and to permit escape of air from the vacuum or negative pressure region 24 at its upper end simply by means a stopper or a closure piece or other suitable sealing arrangement, in order then to close the flow path through the rod 20 to make available the desired vacuum or the desired negative pressure region 24.

FIG. 6 shows a valve arrangement in accordance with one embodiment of the present disclosure, the valve arrangement being inexpensive to produce and yet able to fulfil the desired function. The surrounding wall of the head 18 can be seen according to FIG. 6*a*. The head is provided with a hole, which here represents a valve opening. The valve 30, which can correspond to the valve according to FIG. 5*a*, has a valve opening 30*a*. The valve opening 30*a* is sealed by a membrane 30*b*, wherein the membrane is adhesively bonded on the left-hand side to the valve head for example, or is secured by a securing structure or feature 30*c*. On the opposite side, the valve membrane 30*b* is in contact with a contact seal 30*d* which, for example, can be made of silicone, rubber or plastic. In a starting state according to FIGS. 6*a* and 6*b*, the valve film or valve membrane 30*b*, held by a securing means 30*c*, bears on the contact seal 30*d* and will close the opening 30*a* in the rest position.

Figure 6A:
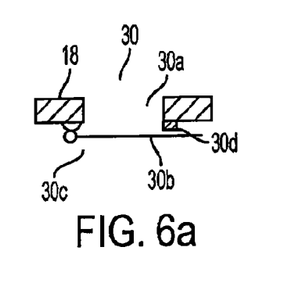
Figure 6B:
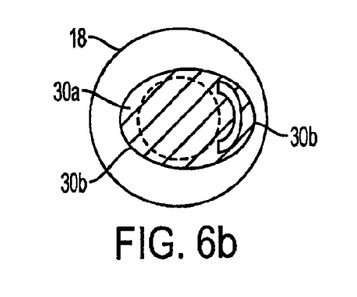
Figure 6C:
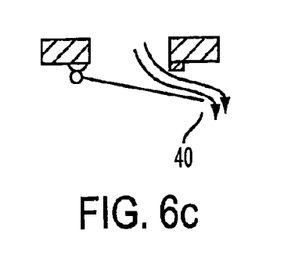
Figure 6D:
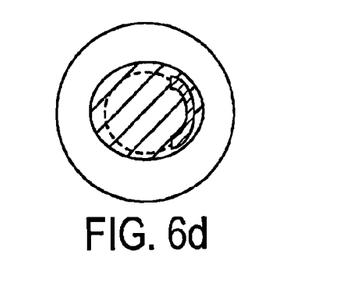

If the valve head is now inserted into the volume 14, the valve membrane 30*b* according to FIG. 6*c* is deflected by the overpressure within the air or gas volume 23, and the air can escape from the hollow space between the stopper 16 and the head 18. As can be seen from FIGS. 6*c* and 6*d*, the valve membrane 30*b* previously in contact with the contact seal 30*d* lifts away from the contact seal 30*d*, for example by pretensioning of the valve membrane 30*b*. The outlet deformation 40 for the valve membrane 30*b* thus permits the desired function, which is intended to permit the escape of an overpressure between the head 18 and the stopper 16.

Figure 6E:
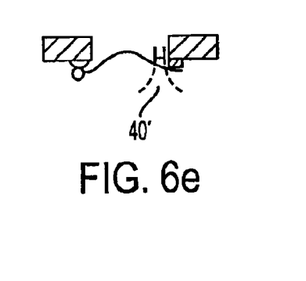
Figure 6F:
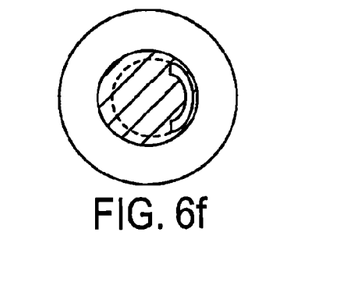

After the air has escaped, and as soon as the valve head 18 is pulled, an overpressure acts from outside on the valve membrane 30*b* according to FIGS. 6*e* and 6*f*, which leads to a sealing or closing deformation 40' for the valve membrane 30*b*. The desired low-pressure region or vacuum region 24 can now be made available between the head 18 and the stopper 16.

Embodiments of the present invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An injection device comprising: a first volume for accommodating a product for administration, a piston for acting upon the product within the first volume, and a stopper disposed between an end of the piston facing the product and the product within the first volume, a second volume being defined between the stopper and the end of the piston facing the product, wherein the piston comprises a piston head configured such that when the piston is advanced in an administration direction, fluid outflow is permitted from the second volume in a direction generally opposite the administration direction and wherein the piston head is separate from the stopper such that a negative pressure or vacuum region can be developed in the second volume.

2. The injection device as claimed in claim 1, wherein the piston head further comprises a sealing lip extending about the full circumference of the piston head and which provides a substantially gas-tight seal with respect to a wall of the first and/or second volumes.

3. The injection device as claimed in claim 2, wherein the sealing lip comprises a predetermined leakage arrangement in the administration direction.

4. The injection device as claimed in claim 1, the injection device further comprising a piston rod, wherein the piston rod comprises a hollow conduit that can be opened and/or closed.

5. The injection device as claimed claim 2, wherein the sealing lip is designed to be invertible or bendable.

6. The injection device as claimed in claim 5, wherein the piston further comprises a piston rod configured such that when inserted into the first volume, air or gas between the stopper and the piston head can escape.

7. The injection device as claimed in claim 1, wherein the piston head comprises a sealing mechanism.

8. The injection device as claimed in claim 4, wherein at least one of the piston head and piston rod comprise at least one valve.

9. The injection device as claimed in claim 8, wherein the valve is a one-way valve.

10. The injection device as claimed in claim 8, wherein the valve is a two-way valve.

11. The injection device as claimed in claim 8, wherein at least one of the piston head and the piston rod comprise a first valve and a second valve, the first valve having a lower trigger pressure than the second valve, wherein one of first and second valves is active in a first direction and the other is active in a second direction generally opposite the first direction.

12. The injection device as claimed in claim 8, wherein the at least one valve comprises a membrane which is freely movable in an air or gas outlet direction, and wherein the membrane is supported in an air inlet direction and is configured to sealingly bear on a membrane support such that a negative pressure or vacuum region can be developed between the stopper and the piston head.

13. The injection device as claimed in claim 1, wherein the stopper has at least one radial indentation.

14. The injection device as claimed in claim 13, wherein an end of the stopper facing toward the piston head comprises at least one cavity formed in the axial direction of the stopper.

15. An injection device comprising:
    a first volume for accommodating a product for administration,
    a piston for acting upon the product within the first volume in an administration direction, the piston comprising a piston head on a distal end thereof, and
    a stopper disposed between the piston head and the product within the first volume,
    wherein a second volume is defined between the piston head and a proximal end of the stopper, and
    wherein the piston head comprises a outflow permitting structure that is configured such that when the piston head is advanced in the administration direction fluid outflow is permitted from the second volume in a direction generally opposite the administration direction to achieve a negative pressure region in the second volume, thereby reducing movements of the stopper in the administration direction independent of movement of the piston.

16. The injection device as claimed in claim 15, wherein the piston head and the first and second volumes are configured such that the negative pressure region is maintained substantially throughout movement of the stopper from an initial position to a final position in which the product has been substantially emptied from the first volume.

17. The injection device as claimed in claim 15, wherein the outflow permitting structure comprises a sealing lip.

18. The injection device as claimed in claim 15, wherein the outflow permitting structure comprises a valve.

* * * * *

UNITED STATES PATENT AND TRADEMARK OFFICE
CERTIFICATE OF CORRECTION

| | | |
|---|---|---|
| PATENT NO. | : 8,622,956 B2 | Page 1 of 2 |
| APPLICATION NO. | : 12/392425 | |
| DATED | : January 7, 2014 | |
| INVENTOR(S) | : Ivan Heutschi | |

It is certified that error appears in the above-identified patent and that said Letters Patent is hereby corrected as shown below:

In the Specification

Col. 1, Line 34,
"requirements. It some embodiments, the present disclosure" should read
--requirements. In some embodiments, the present disclosure--;

Col. 2, Line 40,
"into the volume, the sealing lip is able to snap round counter" should read
--Into the volume, the sealing lip is able to snap around counter--;

Col. 5, Line 25,
"the product or substance to be delivered amounts to approxi-" should read
--of the product or substance to be delivered amounts to approxi- --;

Col. 6, Line 30,
"configuration may have a cylinder summetry, but can config-" should read
--configuration may have a cylinder summetry, but can be config- --;

Col. 7, Line 41,
"tive pressure region 24 at its upper end simply by means a" should read
--tive pressure region 24 at its upper end simply by means of a--;

In the Claims

Col. 8, Claim 5, Line 55,
"The injection device as claimed claim 2, wherein the" should read
--The injection device as claimed in claim 2, wherein the--; and Signed and Sealed this
Seventeenth Day of February, 2015

Michelle K. Lee
*Deputy Director of the United States Patent and Trademark Office*

Col. 10, Claim 15, Line 5,
"wherein the piston head comprises a outflow permitting" should read
--wherein the piston head comprises an outflow permitting--.